(12) United States Patent
Imai

(10) Patent No.: US 10,444,182 B2
(45) Date of Patent: Oct. 15, 2019

(54) SEMICONDUCTOR DEVICE

(71) Applicant: Kabushiki Kaisha Toshiba, Minato-ku, Tokyo (JP)

(72) Inventor: Kaita Imai, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 262 days.

(21) Appl. No.: 15/459,414

(22) Filed: Mar. 15, 2017

(65) Prior Publication Data
US 2017/0269024 A1  Sep. 21, 2017

(30) Foreign Application Priority Data
Mar. 16, 2016 (JP) .................. 2016-052439

(51) Int. Cl.
*G01R 31/26* (2014.01)
*G01N 27/414* (2006.01)
*G01N 27/416* (2006.01)

(52) U.S. Cl.
CPC ..... *G01N 27/4148* (2013.01); *G01N 27/4167* (2013.01)

(58) Field of Classification Search
CPC .......... G01R 31/26; G01R 1/30; G01R 23/02; G01R 27/025; G01R 27/08; G01R 27/205; G01R 27/22; G01R 29/0878; G01R 29/12; G01R 31/001; G01R 31/005
USPC ......... 324/760.02, 762.08, 762.09, 768, 769, 324/762.01, 762.05, 719, 758.05, 446, 324/447, 448, 449
See application file for complete search history.

(56) References Cited

U.S. PATENT DOCUMENTS

| | | | |
|---|---|---|---|
| 6,856,161 B2 | 2/2005 | Thewes | |
| 8,217,433 B1 | 7/2012 | Fife | |
| 2002/0006632 A1* | 1/2002 | Ponnampalam | G01N 33/544 435/7.92 |
| 2009/0026082 A1* | 1/2009 | Rothberg | C12Q 1/6869 204/556 |
| 2009/0052256 A1 | 2/2009 | Sutardja | |
| 2010/0033362 A1 | 2/2010 | Kitami | |
| 2010/0211364 A1* | 8/2010 | Mandal | G05B 17/02 703/2 |
| 2011/0032401 A1 | 2/2011 | Nikai | |

(Continued)

FOREIGN PATENT DOCUMENTS

| | | |
|---|---|---|
| JP | 2000-055874 A | 2/2000 |
| JP | 4137239 B2 | 8/2008 |

(Continued)

OTHER PUBLICATIONS

Y. Liu et al., "Minimal Readout Scheme for ISFET Sensing Arrays Based on Pulse Width Modulation," IET, vol. 48, No. 10, pp. 548-549, May 10, 2012.

*Primary Examiner* — Jermele M Hollington
*Assistant Examiner* — Taqi R Nasir
(74) *Attorney, Agent, or Firm* — White & Case LLP

(57) ABSTRACT

According to one embodiment, a semiconductor device includes FET having a threshold changing according to a chemical state in a gate portion, a time-varying signal application section configured to apply a time-varying signal to at least one of a source, a drain and a back gate of the FET, and a signal reading section configured to read a change in the threshold of the FET resulting from the application of the time-varying signal as a signal.

15 Claims, 16 Drawing Sheets

(56) References Cited

U.S. PATENT DOCUMENTS

| | | | |
|---|---|---|---|
| 2012/0001646 A1* | 1/2012 | Bolander | G01R 31/2621 |
| | | | 324/679 |
| 2013/0015329 A1 | 1/2013 | Iwaki | |
| 2013/0252828 A1* | 9/2013 | Georgiou | C12Q 1/6825 |
| | | | 506/2 |
| 2014/0093881 A1* | 4/2014 | Sugnet | H03M 7/30 |
| | | | 435/6.12 |
| 2014/0235452 A1* | 8/2014 | Rothberg | G01N 27/4148 |
| | | | 506/2 |
| 2016/0300240 A1* | 10/2016 | Bright | G06Q 30/018 |
| 2017/0074797 A1 | 3/2017 | Imai et al. | |

FOREIGN PATENT DOCUMENTS

| | | |
|---|---|---|
| JP | 2011-215105 A | 10/2011 |
| JP | 2014-508915 A | 4/2014 |
| JP | 2017-058163 A | 3/2017 |
| WO | 2016-104517 A1 | 6/2016 |

\* cited by examiner

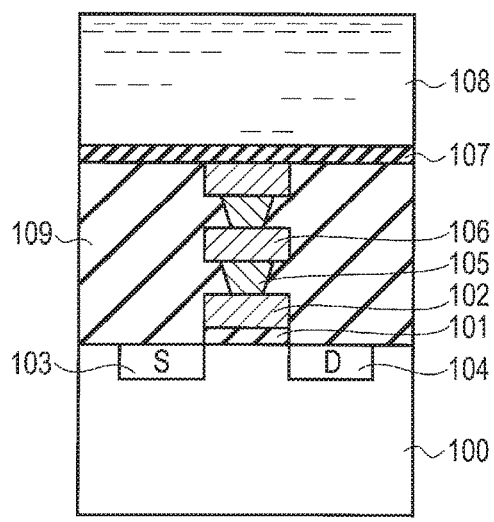
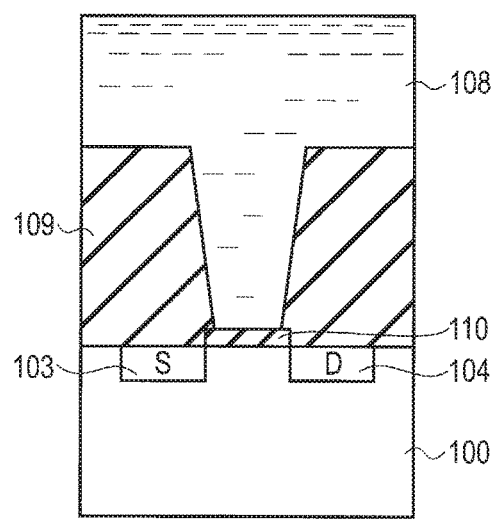
F I G. 3A              F I G. 3B

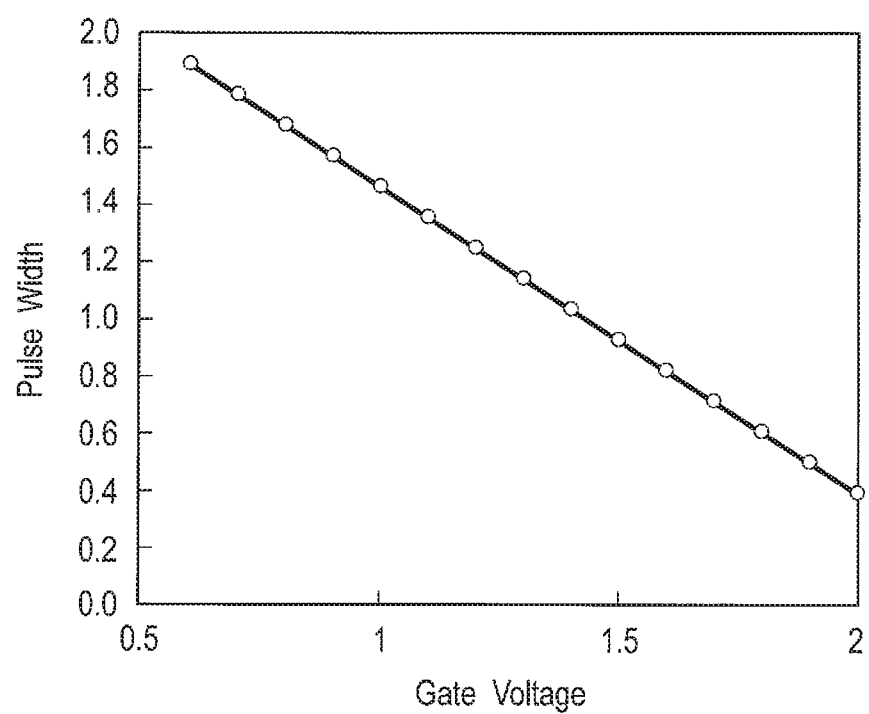
F I G. 10

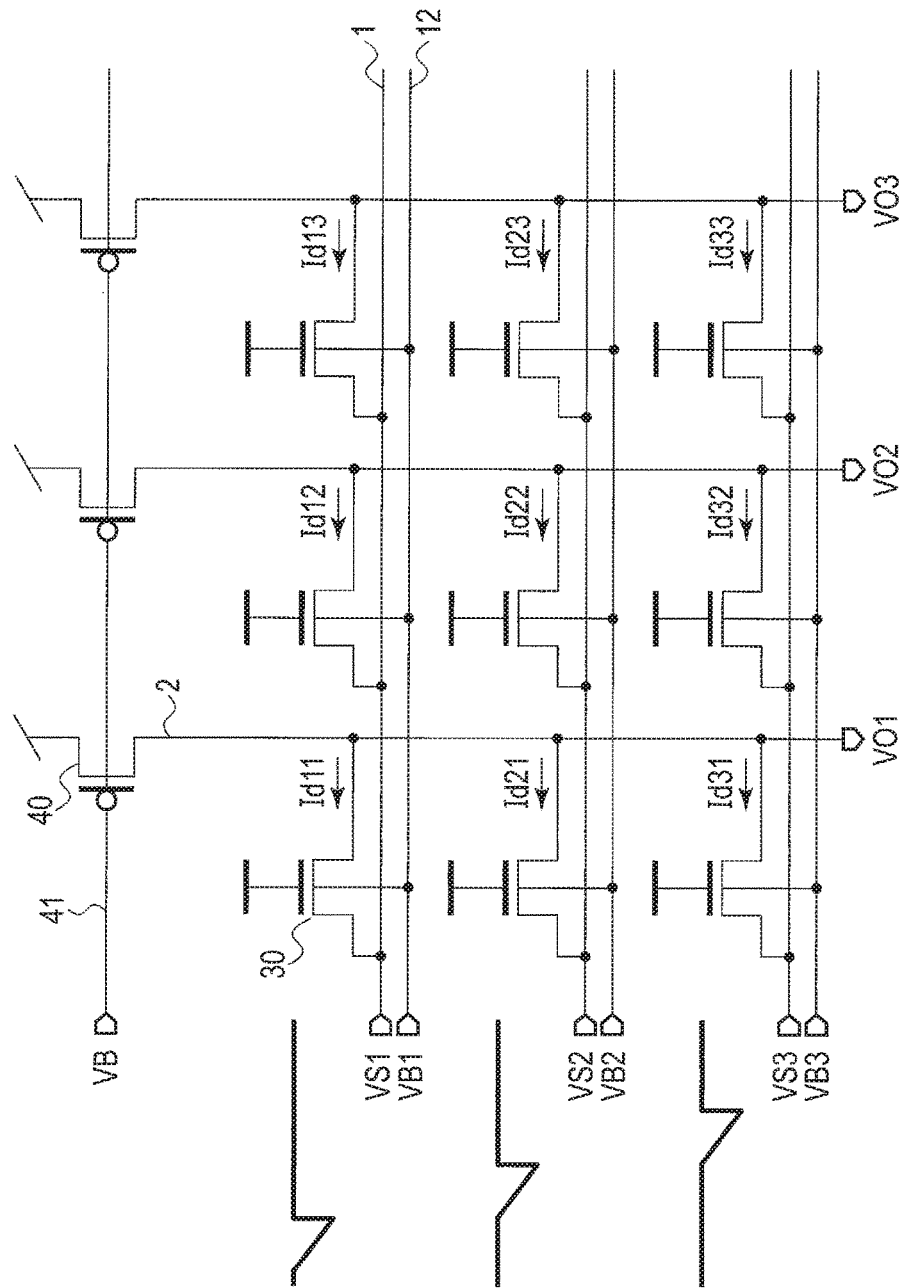
F I G. 11

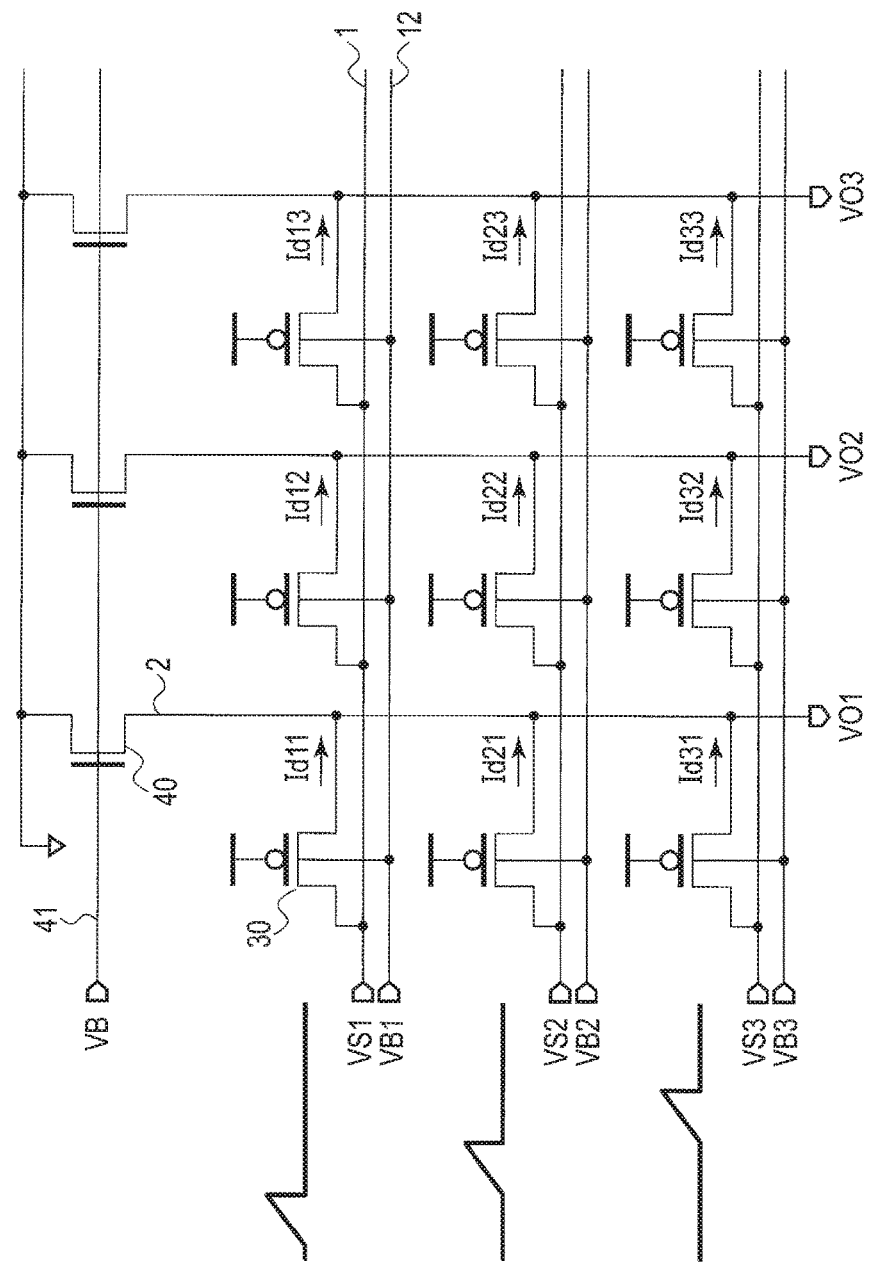
F I G. 12

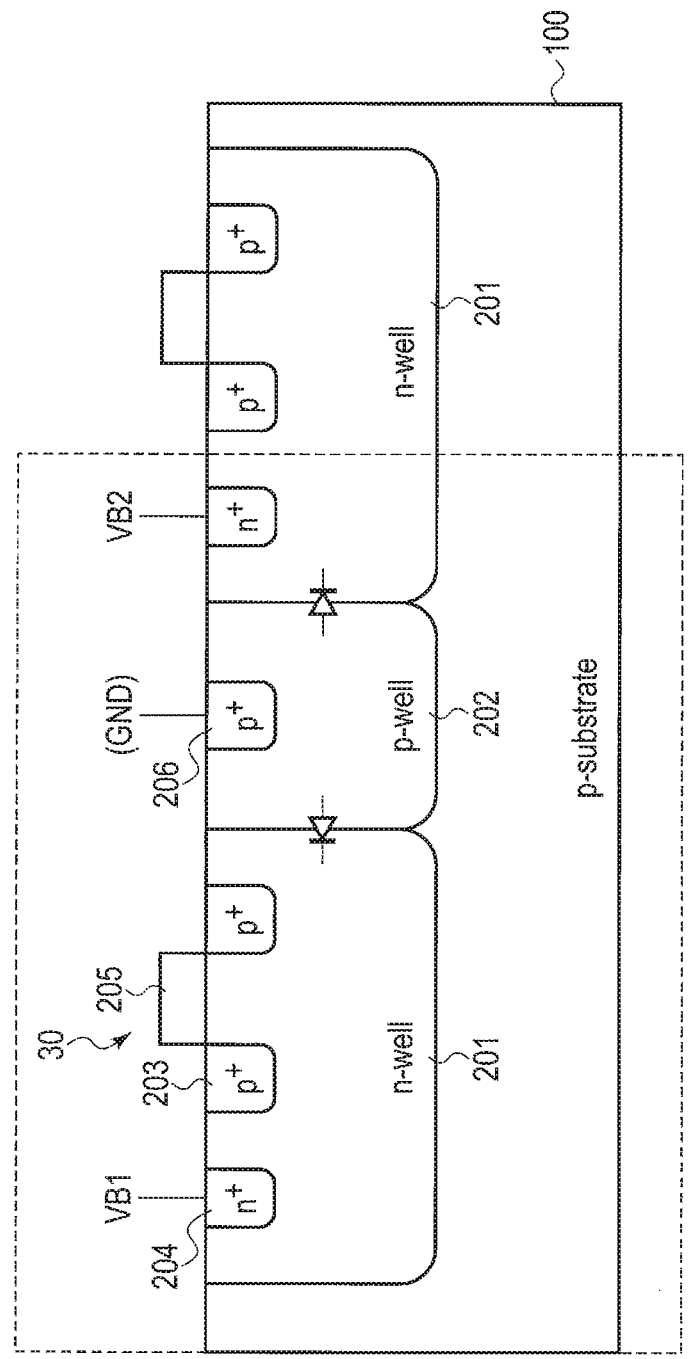
F I G. 15

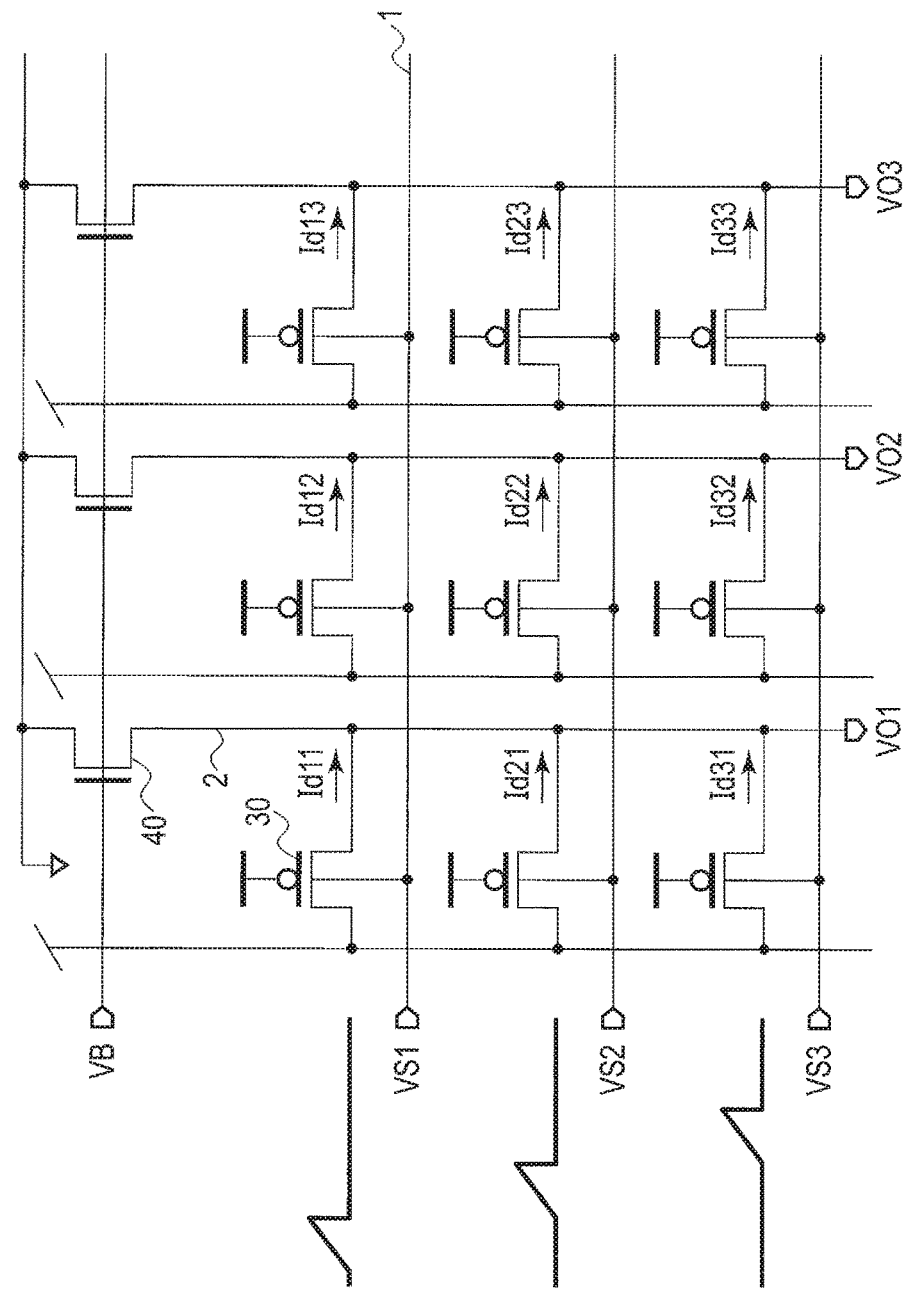
F I G. 16

SEMICONDUCTOR DEVICE

CROSS-REFERENCE TO RELATED APPLICATIONS

This application is based upon and claims the benefit of priority from Japanese Patent Application No. 2016-052439, filed Mar. 16, 2016, the entire contents of which are incorporated herein by reference.

FIELD

Embodiments described herein relate generally to a semiconductor device configured to detect chemical characteristics of a sample.

BACKGROUND

In recent years, as one of chemical field-effect transistors (Chem-FETs), an ion-sensitive field-effect transistor (ISFET) configured to detect a change in a chemical substance such as a hydrogen ion or the like now receives attention. Further, recently, a time width modulation type ISFET configured to apply a time-varying signal such as a ramp wave or the like to a dual gate to thereby output a chemical state as a pulse width is proposed.

BRIEF DESCRIPTION OF THE DRAWINGS

FIG. 3A and FIG. 3B are cross-sectional views showing the device structure of an ISFET used in the semiconductor measurement device of FIG. 2.

FIG. 10 is a characteristic diagram showing a relationship between a gate voltage and a pulse width of an ISFET.

FIG. 11 is a circuit configuration diagram showing a semiconductor measurement device according to a fourth embodiment.

FIG. 12 is a circuit configuration diagram showing another example of the semiconductor measurement device according to the fourth embodiment.

FIG. 15 is a cross-sectional view taken along line I-I' of FIG. 14.

FIG. 16 is a circuit configuration diagram showing a semiconductor measurement device according to a fifth embodiment.

DETAILED DESCRIPTION

In general, according to one embodiment, there is provided a semiconductor device comprising: FET having a threshold changing according to a chemical state in a gate portion; a time-varying signal application section configured to apply a time-varying signal to at least one of a source, a drain and a back gate of the FET; and a signal reading section configured to read a change in the threshold of the FET resulting from the application of the time-varying signal as a signal.

Hereinafter, semiconductor devices according to embodiments will be described with reference to the accompanying drawings.

First Embodiment

Figure 1:
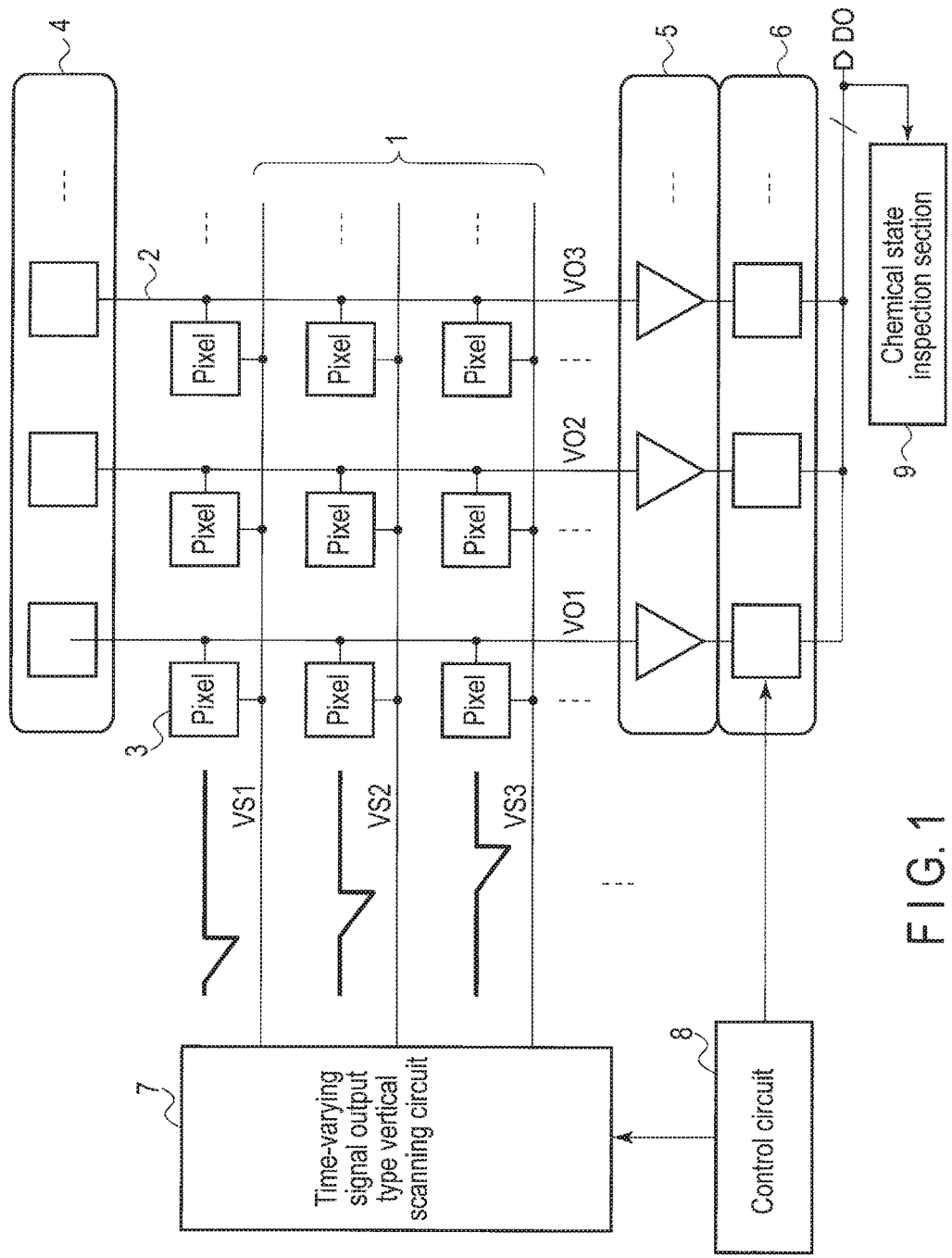
FIG. 1 is a block diagram showing the basic configuration of a semiconductor measurement device according to a first embodiment.

FIG. 1 is a block diagram showing the basic configuration of a semiconductor measurement device according to a first embodiment. A plurality of horizontal signal lines 1 are arranged in parallel with each other. A plurality of vertical signal lines 2 are arranged in parallel with each other to be perpendicular to the horizontal signal lines 1. Further, pixels 3 are arranged at intersections of the horizontal signal lines 1 and the vertical signal lines 2. That is, the pixels 3 are arranged two-dimensionally in a matrix form, and constitute a pixel array. Each of the pixels 3 is formed of a Chem-FET such as an ISFET or the like a threshold of which changes according to a change in concentration of a chemical substance such as a hydrogen ion or the like.

The Chem-FET is a semiconductor sensor configured to sense, for example, an ion such as $H^+$, $K^+$, $Ca^{2+}$ or the like, neurotransmitter such as acetylcholine or the like, metabolite such as a metabolic product produced inside cells or outside cells or a substance which can be metabolized, specific antigen or antibody, or protein derived from the antigen or antibody, and so on. Further, the Chem-FET converts a signal based on information originating from a chemical substance to be detected into an electrical signal.

An end of each of the vertical signal lines 2 is connected to a current source 4, and the other end thereof is connected to an edge detection circuit (inversion timing detection circuit) 5. The current source 4 is constituted of, for example, a current mirror circuit. Here, in the case of a source-grounded amplifier in which an nMOS is used as a pixel 3, the current source 4 is a pMOS current mirror circuit. In the case of a source-grounded amplifier in which a pMOS is used as a pixel 3, the current source 4 is an nMOS current mirror circuit. Further, in the case of a source follower amplifier using an nMOS as a pixel 3, the current source 4 is an nMOS current mirror circuit. In the case of a source follower amplifier using a pMOS as a pixel 3, the current source 4 is a pMOS current mirror circuit. The edge detection circuit 5 is constituted of, for example, comparators, and detects inversion timing (pulse edge) of a pixel output appearing on a vertical signal line 2.

An output signal of the edge detection circuit 5 is supplied to a pulse width detection circuit (time measurement circuit)

6. The pulse width detection circuit 6 is constituted of, for example, counters, and counts an amount of time from the predetermined time to the time when the pixel output is inverted on the basis of the output signal of the edge detection circuit 5.

A measurement signal of the pulse width detection circuit 6 is supplied to a chemical state inspection section 9. This chemical state inspection section 9 is configured to inspect a chemical state of a setting region of the pixel 3 on the basis of the measurement signal of the pulse width detection circuit 6.

An end of each of the horizontal signal lines 1 is connected to a time-varying signal output type vertical scanning circuit 7. The vertical scanning circuit 7 applies a time-varying signal such as a ramp wave or the like changing in the amplitude with the lapse of time to the horizontal signal lines 1 in sequence. Further, a control circuit 8 controls operations of the vertical scanning circuit 7 and the counters 6.

Next, the specific configuration and operation of the semiconductor measurement device of this embodiment will be described below with reference to FIG. 2 through FIG. 6.

Figure 2:
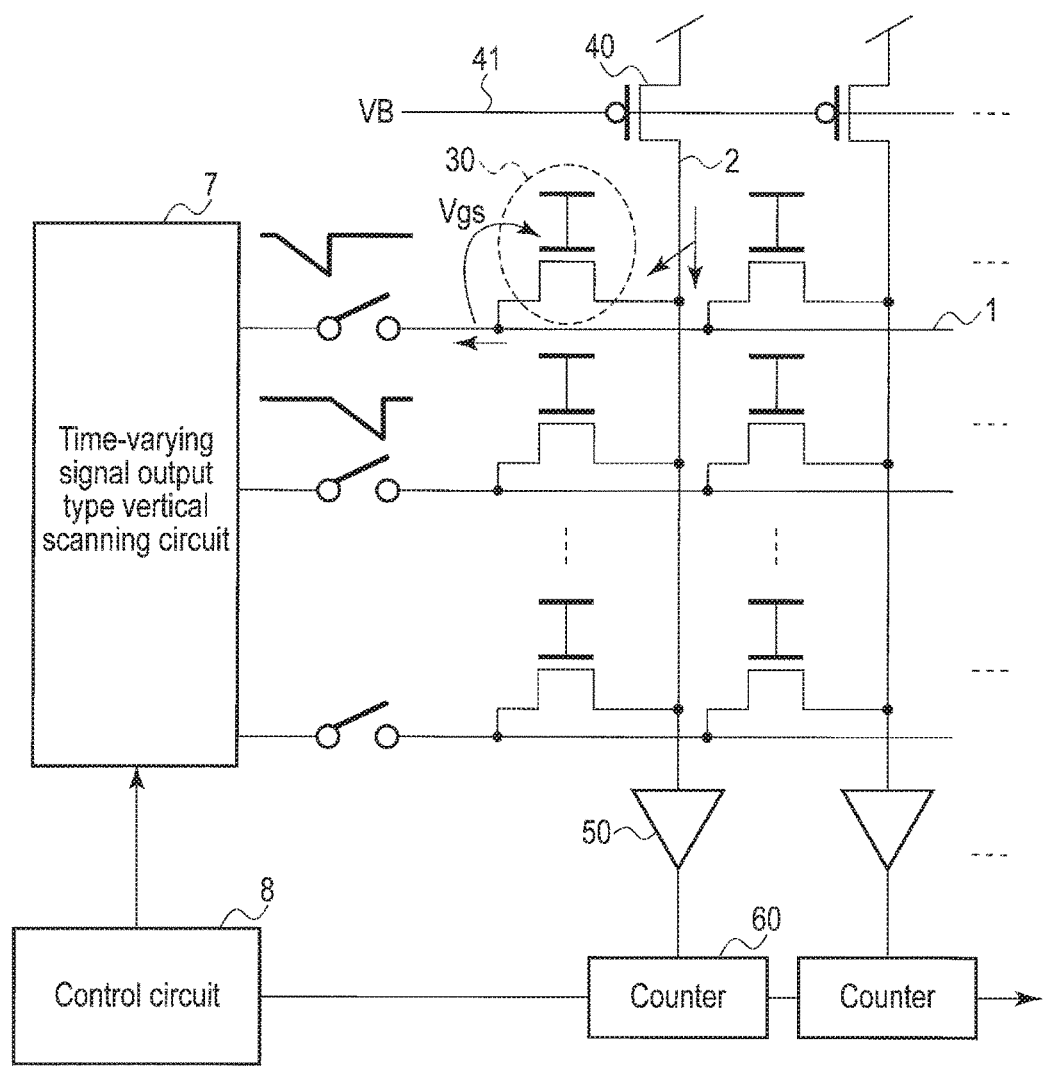
FIG. 2 is a circuit configuration diagram showing a specific configuration example of a semiconductor measurement device according to the first embodiment.

FIG. 2 is a circuit configuration diagram showing the semiconductor measurement device of FIG. 1 in a further concretizing manner.

The pixel 3 is constituted of, for example, an ISFET 30 configured to detect a concentration of a specific ion. In each of the pixels 3, a source of the ISFET 30 is connected to a horizontal signal line 1, and a drain is connected to a vertical signal line 2. It should be noted that in order to detect not a concentration of the specific ion, but a concentration of another chemical substance, another Chem-FET may be employed. The circuit configuration of this case is identical to that of the ISFET 30.

Examples of the ISFET 30 are shown in FIG. 3A and FIG. 3B. FIG. 3A shows a configuration called that of an extended-gate type. The extended-gate type configuration is a configuration in which an ion-sensitive membrane is connected to a gate of a MOS structure FET through a contact via, and a threshold of which changes according to an ion concentration of a sample in contact with the ion-sensitive membrane. More specifically, a gate electrode 102 is formed on a substrate 100 through a gate insulating film 101, and source/drain regions 103 and 104 are formed on both sides of the gate electrode 102. Thereby, a MOSFET is formed. Contacts 105 and metallic layers 106 are alternately formed on the gate electrode 102, and an ion-sensitive membrane 107 is formed on the metallic layer 106 of the uppermost layer. The total number of the metallic layers 106 is determined in consideration of the number, and the like of wiring layers needed to form an integrated circuit. Further, the ion-sensitive membrane 107 is in contact with a sample liquid 108.

As the ion-sensitive membrane 107, for example, when hydrogen ions are to be detected, SiN, TaO or the like is selected. Other ions can be detected by using an ion-sensitive membrane employing a polymeric membrane as a base material, and containing ionophore capable of selecting the ions to be detected from among other singular types of ions. Examples of the polymeric membrane include polyvinyl chloride and PENIS. Examples of ionophore include $Na^+$: bis(12-crown-4), $K^+$: bis(benzo-15-crown-5), valinomycin, $Ca^+$: K23E1, and $NH4^+$: TD19C6.

FIG. 3B is a configuration called that of an open-gate type. In the open-gate type configuration, a gate oxide film of the MOS structure is in direct contact with the sample. More specifically, a gate insulating film 110 is formed on a substrate 100. By using SiN or TaO as the gate insulating film 110, the film 110 functions as an ion-sensitive membrane of a hydrogen ion. Furthermore, by using, as the gate insulating film 110, an ion-sensitive membrane employing a polymeric membrane as a base material, or forming such an ion ion-sensitive membrane on the gate insulating film 110, ions other than the hydrogen ion can be detected. On both sides of the gate insulating film 110, source/drain regions 103 and 104 are formed. Thereby, a MOSFET is formed.

It should be noted that in FIG. 3A and FIG. 3S, the source/drain regions 103 and 104 are respectively connected to peripheral circuits through contacts not shown.

As the current source 4, for example, a p-type MOSFET (current load) 40 whose gate is supplied with a bias voltage VB from a bias signal line 41 is used. By this current load 40, when the ISFET 30 is in an off-state, the potential of the vertical signal line 2 is made constant ("H" level). As the edge detection circuit 5, each of comparators 50 an output of which is inverted when comparison with a reference level is carried out is used. As the pulse width detection circuit 6, each of counters 60 configured to count an amount of time elapsed from the predetermined time is used.

Figure 4:
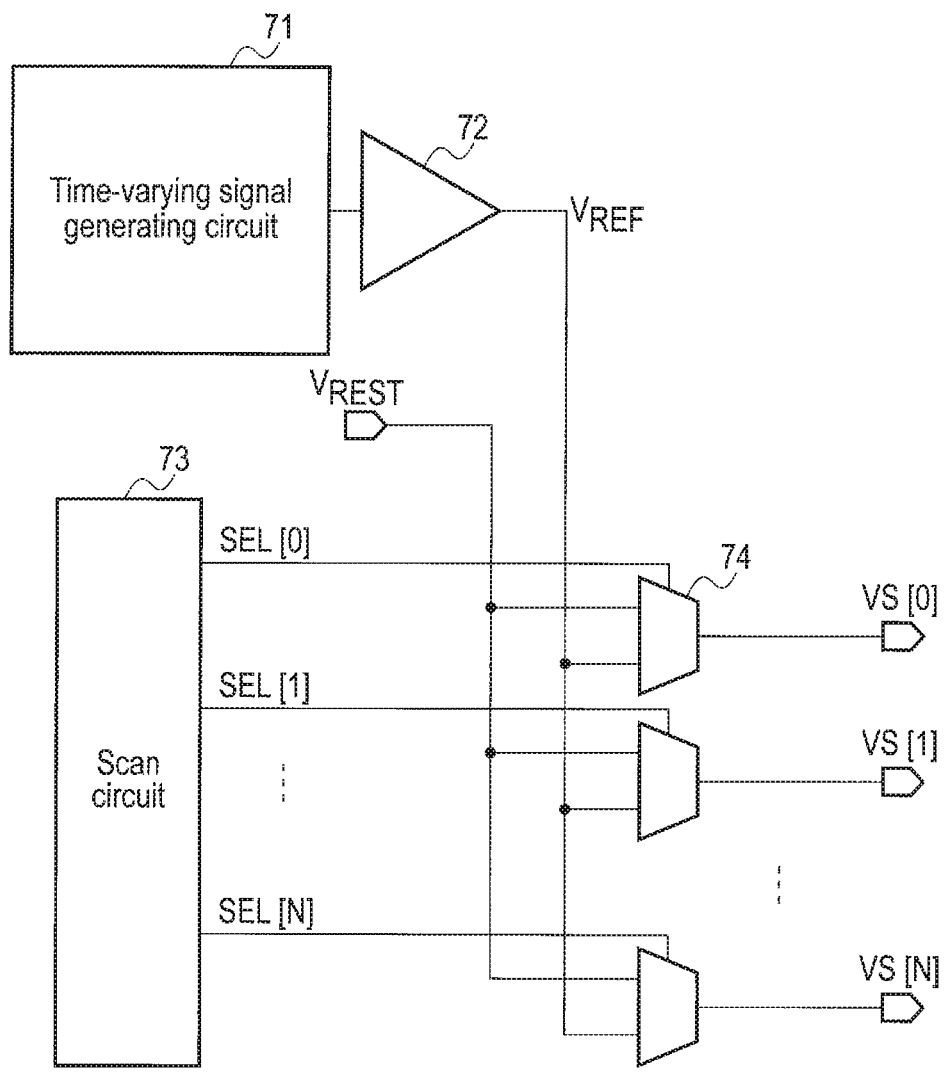
FIG. 4 is a circuit configuration diagram showing a vertical scanning circuit used in the semiconductor measurement device of FIG. 2.

The vertical scanning circuit 7 can be constituted of, as shown in, for example, FIG. 4, a time-varying signal generating circuit 71, driver amplifier 72, scan circuit 73, and selectors 74. The time-varying signal generating circuit 71 outputs a ramp signal at regular intervals. Further, the driver amplifier 72 outputs a ramp signal $V_{REF}$. The ramp signal $V_{REF}$ is supplied to one input port of each selector 74. A standby voltage $V_{REST}$ is supplied to the other input port of each selector 74. A scan signal SEL from the scan circuit 73 is supplied to a control terminal of each selector 74.

Figure 5:
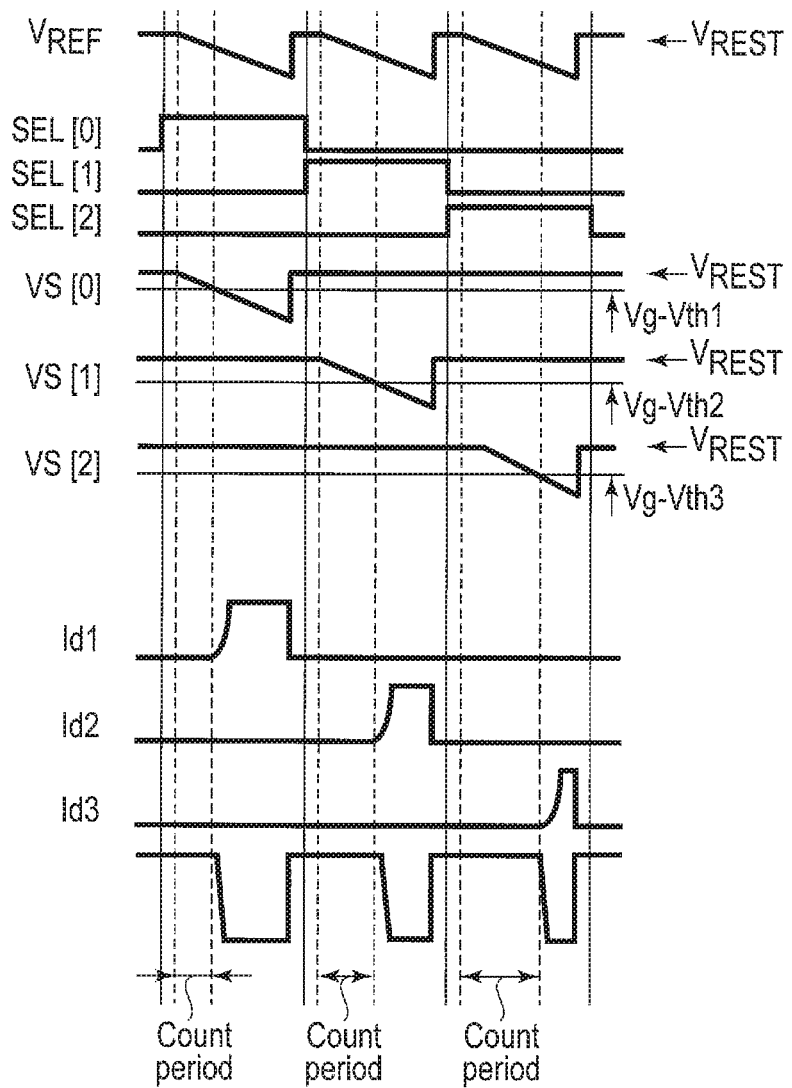
FIG. 5 is a signal waveform chart showing operation waveforms of the corresponding parts of the vertical scanning circuit of FIG. 4.

As shown in FIG. 5, the scan circuit 73 outputs square waves, i.e., row selection signals SEL[0], SEL[1], . . . , SEL[N] in the order mentioned. Thereby, the selectors 74 each output ramp signals VS[0], VS[1], . . . , VS[N] one cycle deviating from each other. Here, although the row selection signals SEL are given one after another in sequence, output of the row selection signals may be started from an arbitrary row or the row selection signals may be output to every other row at intervals. Furthermore, an arbitrary blanking period may be provided after a row selection signal of a certain row has fallen and until the next row selection signal rises.

It should be noted that the switches in FIG. 2 are equivalently shown in order to indicate that a ramp signal VS is alternatively supplied to a plurality of horizontal signal lines 1. These switches may be ones to be incorporated in the scanning circuit 7 or may not be specially provided.

In such a configuration described above, in a state where the ion-sensitive membrane 107 is made in contact with the sample liquid 108, the scanning circuit 7 and the counters 60 are driven according to an instruction from the control circuit 8. Thereby, a ramp signal VS is applied from the vertical scanning circuit 7 to a source end of the ISFET 30 of the first row. The potential of the ramp signal VS gradually lowers, and hence the gate-source potential Vgs of the ISFET 30 gradually becomes larger. Then, when the potential Vgs exceeds the threshold of the ISFET 30, the ISFET 30 is brought into the on-state. At this time, the current is extracted from the vertical signal line 2 toward the vertical scanning circuit 7 side, and the potential of the vertical signal line 2 lowers. That is, the pixel output appearing on the vertical signal line 2 is inverted. The inversion of the pixel output is detected by the comparator 50. Then, the amount of time from the beginning of the ramp signal application to the inversion of the pixel output is counted by the counter 60. This count value corresponds to the threshold of the ISFET 30.

Here, the threshold of the ISFET 30 changes according to the ion concentration of the sample liquid 108. Accordingly, the count value obtained by the counter 60 corresponds to the ion concentration. That is, the ion concentration can be measured by means of the count value of the counter 60. Accordingly, by reading the outputs of the counters 60 in sequence, the ion concentrations corresponding to the pixels 3 of one row can be detected.

By repeating such an operation for the second and subsequent rows, the ion concentrations at all the pixels 3 are detected. That is, the ion concentration distribution of the sample liquid 108 is measured by means of the plurality of ISFETs 30 arranged in a matrix form.

It should be noted that by storing the count values read from the counters 60 in a memory, it is possible to display these values on a display or the like. That is, acquisition and visual display of the ion concentration distribution in the sample is enabled.

As described above, according to this embodiment, a time-varying signal such as a ramp wave or the like is supplied to a source end of the ISFET 30, whereby the output of the pixel 3 is activated, and a change the threshold of the ISFET 30 is binarized in the amplitude direction. Further, a change in the threshold can be read in terms of time-width information. Accordingly, by only carrying out control to make the inclination of the ramp wave gentler or to increase the operation frequency of the counter, the measurement accuracy can easily be changed.

Moreover, in this embodiment, a time-varying signal such as a ramp wave or the like is supplied to the source end of the ISFET 30, and the ISFET 30 requires no dual gate. Accordingly, a particular manufacturing process is unnecessary, and the device can be manufactured at low cost. Furthermore, no dual gate is required, and hence the parasitic capacitance is reduced, and the detection sensitivity can be improved. Further, although the ISFETs 30 are two-dimensionally arranged, selection signal lines used to select rows can be made unnecessary. Therefore, the design freedom is tremendously improved, for example, an advantage that the coverage condition of the wiring layer is moderated can be obtained. Furthermore, the number of transistors for one pixel 3 can be reduced, and thus miniaturization of pixels is enabled.

Second Embodiment

Figure 6:
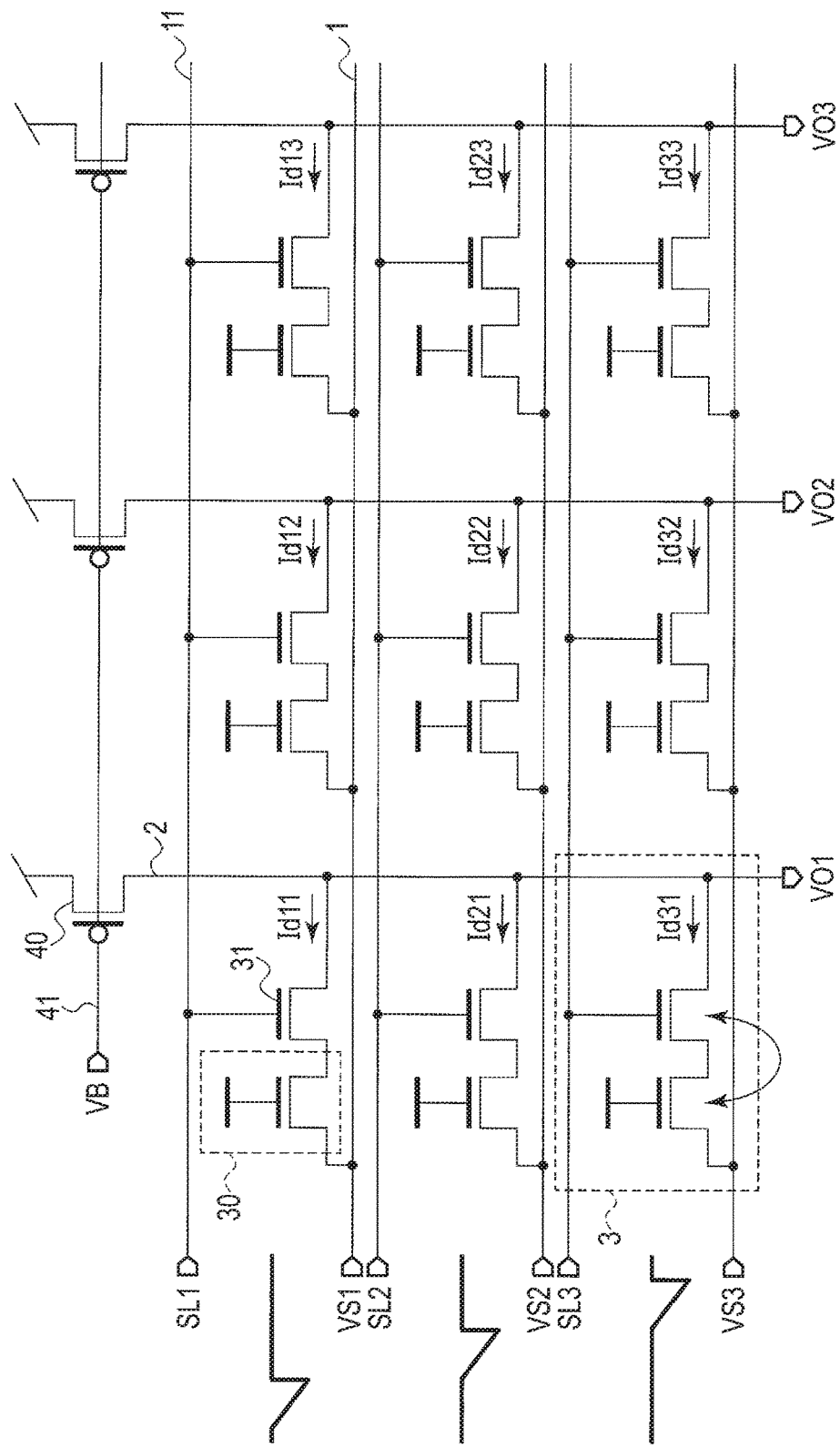
FIG. 6 is a circuit configuration diagram showing a semiconductor measurement device according to a second embodiment.

FIG. 6 is a circuit configuration diagram showing a semiconductor measurement device according to a second embodiment. It should be noted that parts identical to those FIG. 1 and FIG. 2 are denoted reference symbols identical to FIG. 1 and FIG. 2, and detailed descriptions of them are omitted.

What makes this embodiment different from the first embodiment is that a selection transistor configured to select a pixel is provided. That is, a selection transistor 31 is inserted between a drain of an ISFET 30 and a vertical signal line 2. Further, the selection transistor 31 is selected by a horizontal selection signal line 11. The selection transistor prevents a current from flowing backward from the horizontal signal line 1 to the vertical signal line 2 through the unselected ISFET 30. This backflow can occur when the standby voltage $V_{REST}$ deviates from a predetermined value. The case described above is, for example, a case where the voltage $V_{REST}$ is sufficiently greater than the voltage of the vertical signal line 2, and the equivalent gate potential to be applied to the ISFET 30 and including an ion concentration change is lower than VO1.

Here, the horizontal signal line 1 and the horizontal selection signal line 11 are synchronously driven for each row. That is, the ramp signal VS1 and the horizontal selection signal SL1 synchronize with each other, the signal VS2 and the signal SL2 synchronize with each other, and the signal VS3 and the signal SL3 synchronize with each other. Thereby, selection for each row of the ISFETs 30 arranged in a matrix form is enabled.

It should be noted that in this embodiment, although the ISFET 30 has the nMOS configuration, and the current load 40 has the pMOS configuration, conversely, the ISFET 30 may have the pMOS configuration, and the current load 40 may have the nMOS configuration. In this case, it is sufficient if the ramp signal VS is made a signal the potential of which gradually rises contrary to FIG. 5. Further, the insertion position of the selection transistor 31 may be between the drain of the ISFET 30 and the vertical signal line 2 as shown in FIG. 6 or may be between the source of the ISFET 30 and the horizontal signal line 1.

In this embodiment, the horizontal selection signal SL is supplied in synchronism with the ramp signal VS, whereby it is possible to drive the ISFETs 30 in units of rows, and read a change in the threshold of the ISFET 30 in terms of time-width information. Accordingly, an advantage identical to the first embodiment can be obtained. Furthermore, in this embodiment, the selection transistor 31 is provided, whereby it is possible to previously prevent a current from flowing backward from the horizontal signal line 1 to the vertical signal line 2 through the unselected ISFET 30. Therefore, it is possible to improve the freedom of setting the voltage $V_{REST}$ and/or the voltage VR, secure the safety in the experiment, and prevent a malfunction from occurring.

Third Embodiment

Figure 7:
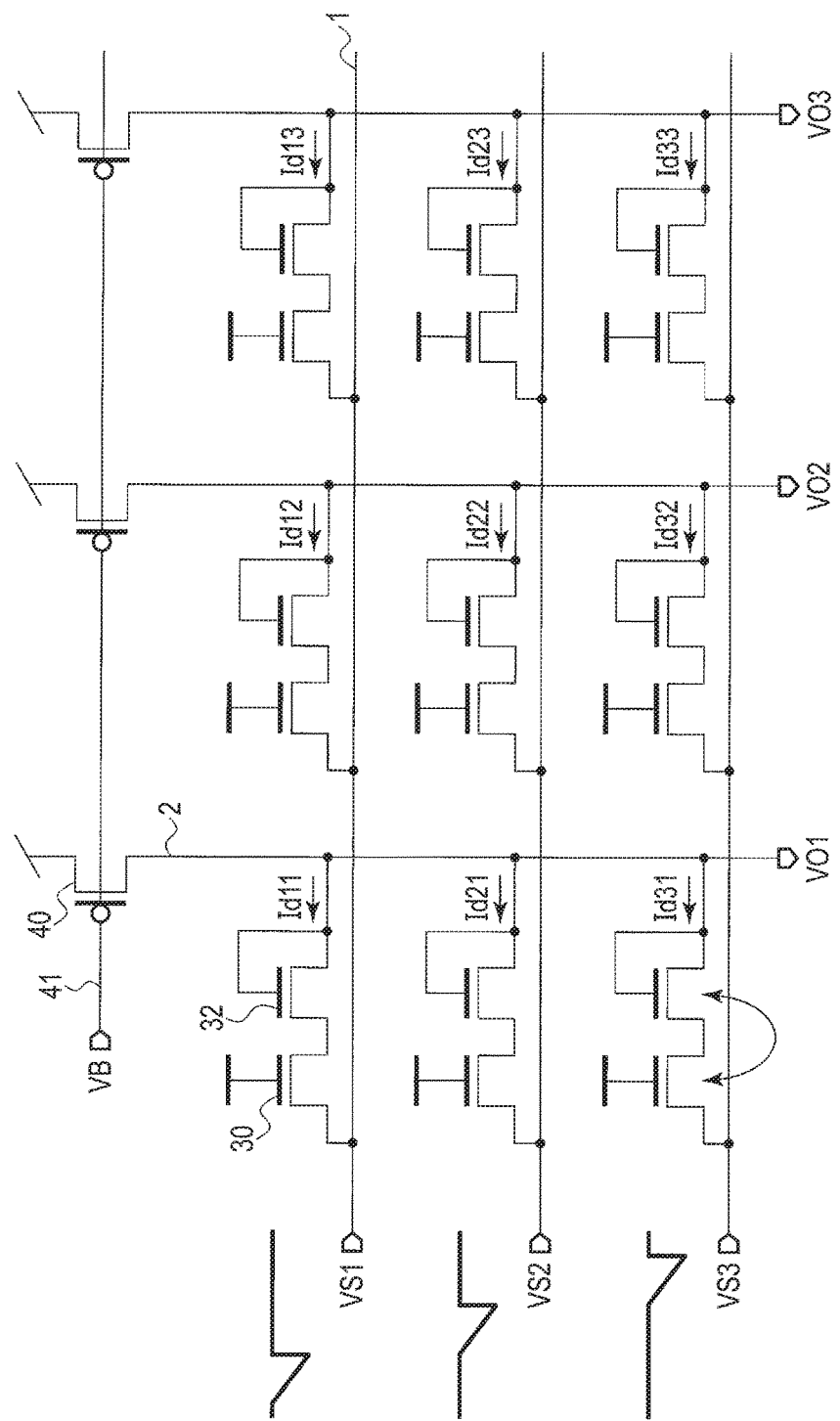
FIG. 7 is a circuit configuration diagram showing a semiconductor measurement device according to a third embodiment.

FIG. 7 is a circuit configuration diagram showing a semiconductor measurement device according to a third embodiment. It should be noted that parts identical to those in FIG. 1 and FIG. 2 are denoted by reference symbols identical to FIG. 1 and FIG. 2, and detailed descriptions of them are omitted.

What makes this embodiment different from the first embodiment is that a diode is provided in series with an ISFET. That is, a diode 32 of the MOS structure is inserted between a drain of an ISFET 30 and a vertical signal line 2. It should be noted that the insertion position of the diode 32 may be between a source of the ISFET 30 and the horizontal signal line 1.

Figure 8:
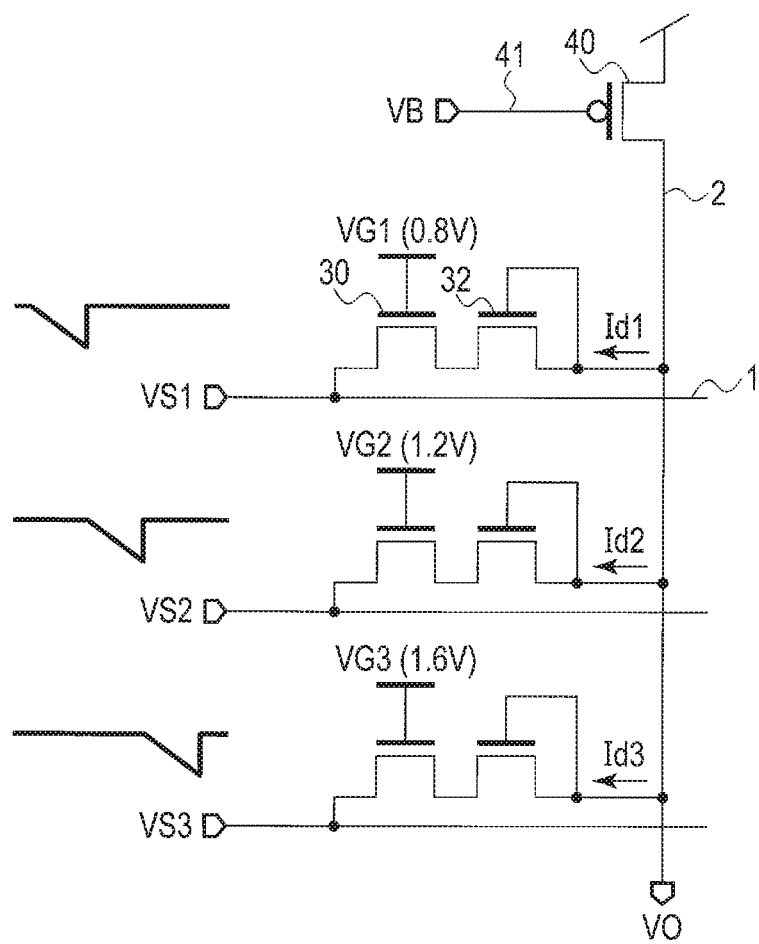
FIG. 8 is a circuit configuration diagram for explaining an operation of the third embodiment, and showing a state where different voltages are applied to gates of ISFETs.

FIG. 8 is a circuit configuration diagram showing a state where different voltages VG1, VG2, and VG3 are applied to gates of three ISFETs 30 connected to the same vertical signal line 2. Here, application of different voltages to the gates is carried out in order to simulate a case where the ion concentrations in the portions of the gates are equivalently different from each other.

Figure 9:
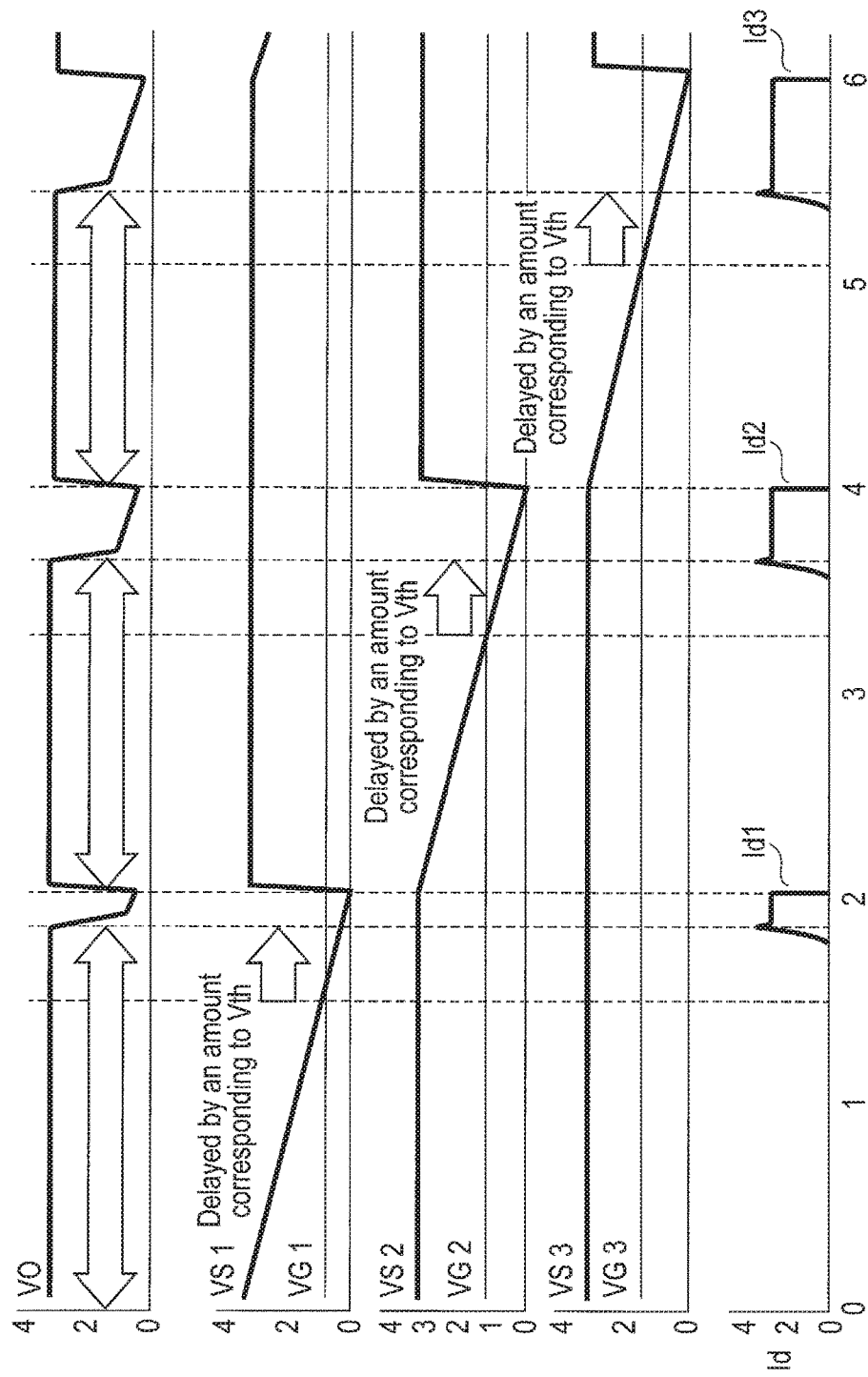
FIG. 9 is a chart for explaining the operation of the third embodiment, and showing temporal changes in voltages VS and VO, and a current Id.

FIG. 9 is a chart showing temporal changes in an input voltage (ramp signal) VS, output voltage VO, and current Id.

As shown in FIG. 8 and FIG. 9, when voltages VS1, VS2, and VS3 are applied in sequence to the sources of the ISFETs 30, the current Id flowing through the vertical signal line 2 are Id1, Id2, and Id3 as shown in FIG. 9. That is, Id1, Id2, and Id3 differ from each other in current rise timing. Further, regarding the voltage VO of the vertical signal line 2, the corresponding portions of the voltage VO differ from each other in voltage fall timing as shown in FIG. 9. That is, as the voltage VG becomes greater, the voltage fall timing of the voltage VO is made earlier in terms of time. In the pulse width detection circuit 6, an amount of time (pulse width) from the start of application of the ramp signal VS to the fall of the voltage VO is detected, and hence the greater the voltage VG, the smaller the pulse width becomes. That is, regarding a relationship between the gate application voltage VG and the pulse width, as the voltage VG becomes greater, the pulse width becomes smaller as shown in FIG. 10.

Accordingly, detecting the output voltage (pixel output) VO of the vertical signal line 2 by means of the edge detection circuit 5 and the pulse width detection circuit 6 makes it possible to obtain signals having different pulse widths resulting from the differences in the gate voltage G. This implies that the pulse width differs depending on a change in the ion concentration in the portion of the gate of the ISFET 30. That is, by detecting the aforementioned pulse width, the ion concentration can be detected.

As described above, in this embodiment too, it is possible to read a change in the threshold of the ISFET 30 in terms of time-width information. Accordingly, an advantage identical to the first embodiment can be obtained. Furthermore, in this embodiment, the horizontal selection signal line 11 is made unnecessary, and hence simplification in the configuration can be more advanced than the second embodiment.

Fourth Embodiment

FIG. 11 is a circuit configuration diagram showing a semiconductor measurement device according to a fourth embodiment. It should be noted that parts identical to those in FIG. 1 and FIG. 2 are denoted by reference symbols identical to FIG. 1 and FIG. 2, and detailed descriptions of them are omitted.

What makes this embodiment different from the first embodiment is that a horizontal selection signal line is connected to a back gate of an ISFET. That is, a horizontal selection signal line 12 for back gate selection is arranged parallel to a horizontal signal line 1. Each horizontal selection signal line 12 is connected to back gates of ISFETs 30 of the same row.

Here, the horizontal signal line 1 and the horizontal selection signal line 12 are synchronously driven for each row. That is, a ramp signal VS1 and a selection signal VB1 synchronize with each other, a signal VS2 and a signal VB2 synchronize each other, and a signal VS3 and a signal VB3 synchronize each other. Thereby, selection for each row of the ISFETs 30 arranged in a matrix form is enabled.

The horizontal selection signal VB is supplied in synchronism with the ramp signal VS, whereby ion concentrations corresponding to pixels 3 of one row are detected. Further, by carrying out ion concentration detection for each row, the ion concentration distribution in the setting region of the ISFETs 30 is measured.

It should be noted that in this embodiment, although the ISFET 30 has the nMOS configuration, and the current load 40 has the pMOS configuration, the ISFET 30 may have the pNOS configuration, and the current load 40 may have the nMOS configuration as shown in FIG. 12.

Figure 13:
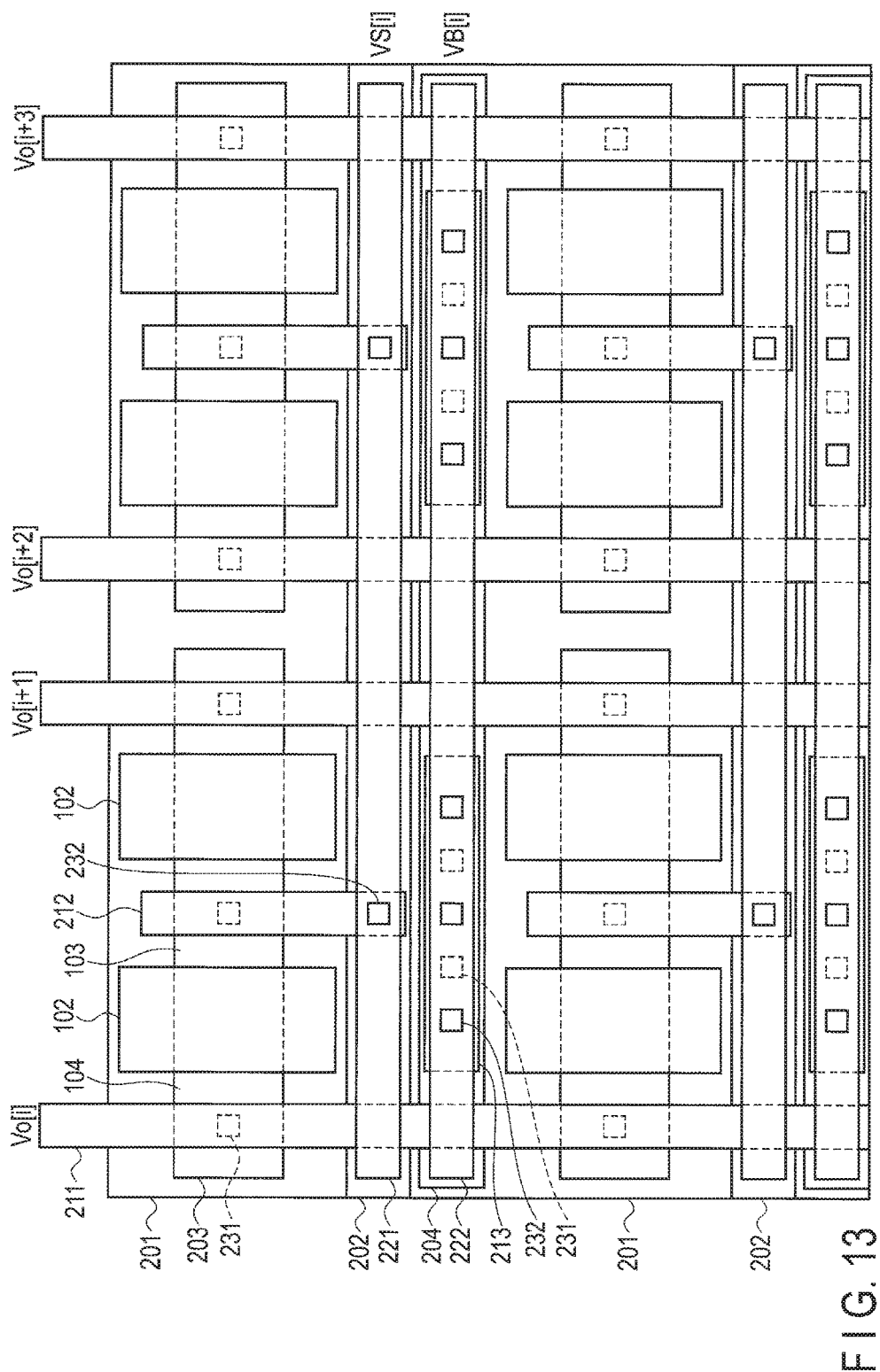
FIG. 13 is a plan view showing an example of the layout of the semiconductor measurement device of the fourth embodiment.

FIG. 13 is a plan view showing an example of the layout of the semiconductor measurement device of FIG. 12.

A reference symbol 201 in FIG. 13 denotes an n-well, 202 denotes a p-well, 203 denotes a p$^+$ region, and 204 denotes an n$^+$ region. It should be noted that at a part at which a gate 102 and the p$^+$ region 203 overlap each other, injection of impurities does not occur in the manufacturing process. The wiring 211 which will become a vertical signal line 2, the wiring 212 to be used to connect a horizontal signal line 1 and a source of an ISFET 30 to each other, and the wiring 213 to be connected to a back gate of the ISFET 30 are formed in the first layer. The wiring 221 which will become the horizontal signal line 1, and the wiring 222 which will become a horizontal selection signal line 12 are formed in the second layer. Further, a reference symbol 231 denotes a contact configured to connect the p$^+$ region 203 or the n$^+$ region 204 and the wiring in the first layer to each other, and 232 denotes a contact configured to connect the wiring in the first layer and the wiring in the second layer to each other. It should be noted that the number of contacts is arbitrary within a range ensuring that their resistance values are sufficiently low.

Figure 14:
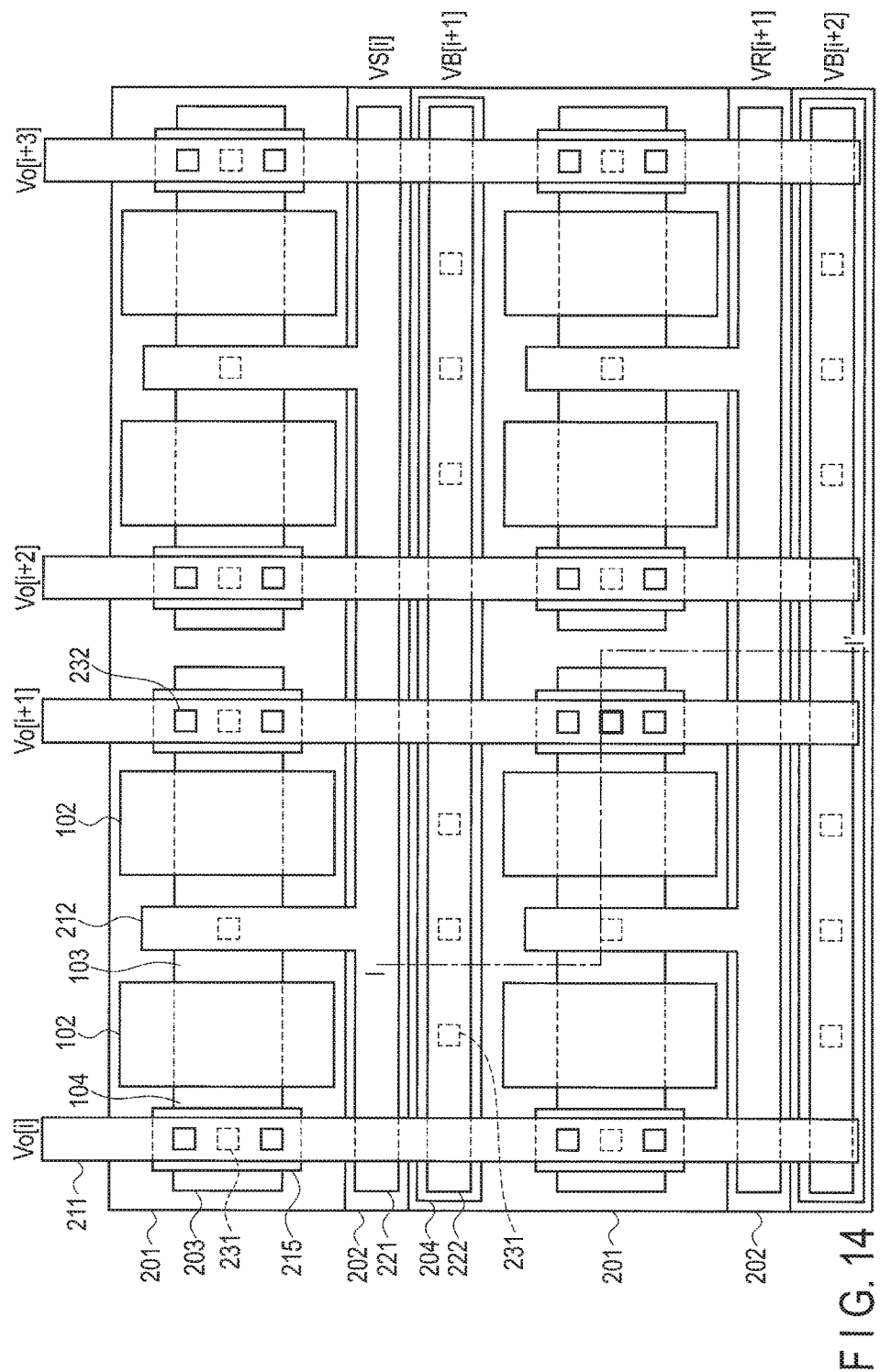
FIG. 14 is a plan view showing another example of the layout of the semiconductor measurement device of the fourth embodiment.

FIG. 14 is a plan view showing another example of the layout of the semiconductor measurement device of FIG. 12. What makes this example different from FIG. 13 is that the wiring 211 is formed in the second layer, and the wiring 221, 222, 212, and 215 other than the wiring 211 are formed in the first layer. That the wiring 221 which will become a horizontal signal line 1, the wiring 222 which will become a horizontal selection signal line 12, the wiring 212 used to connect the horizontal signal line 1 and a source of an ISFET 30 to each other, and the wiring 215 to be connected to a drain of the ISFET 30 are formed in the first layer. Furthermore, only the wiring 211 which will become a vertical signal line 2 is formed in the second layer.

FIG. 15 is a cross-sectional view taken along line I-I' shown in FIG. 14 in an alternate long and short dash line. The part surrounded by a broken line in FIG. 15 corresponds to the range of the alternate long and short dash line in FIG. 14.

In the surface part of a n-substrate 100, n-wells 201 used to form ISFETs are formed in an insular form. Between the adjacent n-wells 201, a p-well 202 for element isolation is formed.

In the surface part of n-well 201, the region 203 (103, 104) that will become source/drain regions and a gate part 205 (101, 102) all of which are used to constitute an ISFET 30 are formed. Furthermore, in the n-well 201, the n$^+$ region 204 to which the back gate potential VB is to be applied is formed. Further, in the surface of the p-well 202, a p$^+$ region 206 is formed. To this p$^+$ region 206, GND is connected.

In such a configuration described above, in the case of a condition (VB1, 2)<<GND, a current can be made to flow owing to a forward bias. On the other hand, in the case of a condition (VB1, 2)>GND, a current does not flow owing to a reverse bias.

According to this embodiment, by applying the horizontal selection signal VB in synchronism with the ramp signal VS, it is possible to drive the ISFETs 30 in units of rows, and read a change in the threshold of the ISFET 30 in terms of time-width information. Accordingly, an advantage identical to the first embodiment can be obtained. Furthermore, in this embodiment, it is possible to previously prevent a current from flowing backward from the horizontal signal line 1 to the vertical signal line 2 through the unselected ISFET 30 without providing a selection transistor. Thereby, it is possible to secure the safety in the experiment, and prevent a malfunction from occurring.

Fifth Embodiment

FIG. 16 is a circuit configuration diagram showing a semiconductor measurement device according to a fifth embodiment. It should be noted that parts identical to those in FIG. 1 and FIG. 2 are denoted by reference symbols identical to FIG. 1 and FIG. 2, and detailed descriptions of them are omitted.

What makes this embodiment different from the first embodiment is that a horizontal signal line is connected to a back gate of an ISFET. That is, a given voltage is applied to a source of an ISFET 30, and a ramp signal VS from a horizontal signal line 1 is input to a back gate of the ISFET 30.

The ramp signal VS is input to the back gate of the ISFET 30, whereby a current corresponding to the threshold of the ISFET 30 flows, and the potential of a vertical signal line 2 changes. Accordingly, it is possible to read a change in the threshold of the ISFET 30 in terms of time-width information. Accordingly, an advantage identical to the first embodiment can be obtained. Further, the horizontal selection signal line 12 is made unnecessary, and hence an advantage that simplification in the configuration can be more advanced than the fourth embodiment is obtained.

MODIFICATION EXAMPLE

It should be noted that the present invention is not limited to the embodiments described above.

In the embodiments, although an ISFET is used to constitute a pixel, the present invention is not limited to this, and an FET capable of detecting chemical characteristics of a sample, i.e., a Chem-EFET can be applied. For example, an enzyme-FET (ENFET) having enzyme sensitivity for detection of organic molecules or an immune-FET (IMFET) having immunity sensitivity for monitoring of immune chemicals can be applied.

The time-varying signal to be applied to the ISFET is not limited to a ramp wave, and a signal having an amplitude changing with time such as a stepped wave, triangular wave, sinusoidal wave, and the like can be used.

The edge detection circuit is not necessarily limited to the comparator, and any circuit capable of detecting inversion timing of a pixel output appearing on a vertical signal line can be used. Furthermore, the pulse width detection circuit is not necessarily limited to the counter, and any circuit capable of measuring an amount of time from the predetermined time to the time when the pixel output is inverted can be employed.

Further, the layout of the circuit, device structure, and the like are by no means limited to FIG. 13 through FIG. 15, and may be appropriately changed according to the specifications.

While certain embodiments have been described, these embodiments have been presented by way of example only, and are not intended to limit the scope of the inventions. Indeed, the novel embodiments described herein may, be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A semiconductor device comprising:
   a pixel array obtained by arranging FETs thresholds of which change according to a chemical state in a gate portion on a substrate in a matrix form;
   a plurality of horizontal signal lines each of which is connected to at least one of a source, a drain and a back gate of each of the FETs in units of rows;
   a vertical scanning circuit configured to alternatively apply a time-varying signal changing in the amplitude with the lapse of time to the plurality of horizontal signal lines;
   a plurality of vertical signal lines each of which is connected to the drain or the source of each of the FETs in units of columns; and
   time measurement circuits each of which is connected to each of the plurality of vertical signal lines, and is configured to measure an amount of time from the predetermined time to the time when an output signal of the FET appearing on the vertical signal line is inverted.

2. The device of claim 1, further comprising a plurality of inversion timing detection circuits each of which is configured to detect inversion timing of an output signal of the FET appearing on the vertical signal line from the predetermined time, wherein
   each of the time measurement circuits measures the amount of time up to the time when the output signal is inverted on the basis of a detection signal of the inversion timing detection circuit.

3. The semiconductor device of claim 1, wherein
   each of the FETs is an ISFET in which an ion-sensitive membrane is connected to a gate electrode, and the ISFET detects an ion concentration of a sample in contact with the ion-sensitive membrane.

4. The device of claim 1, wherein
   the time-varying signal is a ramp wave, a stepped wave, a triangular wave or a sinusoidal wave.

5. The device of claim 1, further comprising a current source configured to supply a given current to each of the vertical signal lines.

6. The device of claim 1, further comprising a switching MOSFET connected in series with each of the FETs between each of the horizontal signal lines and each of the vertical signal lines.

7. The device of claim 1, further comprising a diode connected in series with each of the FETs between each of the horizontal signal lines and each of the vertical signal lines.

8. The device of claim 1, further comprising a chemical state inspection section configured to inspect a chemical state of a setting region of the FETs on the basis of measurement signals of the plurality of time measurement circuits.

9. A semiconductor device comprising:
   pixels arranged on a substrate in a two-dimensional matrix form, the pixels including ISFETs each of which is configured to detect a change in an ion concentration of a sample on each pixel;
   a plurality of horizontal signal lines each of which is connected to a source of each of the ISFETs in units of rows;
   a vertical scanning circuit configured to alternatively apply a time-varying signal changing in the amplitude with the lapse of time to the plurality of horizontal signal lines;
   a plurality of vertical signal lines each of which is connected to a drain of each of the ISFETs in units of columns; and
   a plurality of counters each of which is connected to each of the plurality of vertical signal lines, and measures an amount of time from the time when the time-varying signal is applied to the time when an output of the pixel is inverted.

10. The device of claim 9, further comprising a plurality of edge detection circuits each of which is configured to detect inversion timing of an output of each of the pixels, wherein
each of the counters measures an amount of time up to the time when an output of each of the pixels is inverted on the basis of a detection signal of each of the edge detection circuits.

11. The device of claim 9, wherein
the time-varying signal is a ramp wave, a stepped wave, a triangular wave or a sinusoidal wave.

12. The device of claim 9, further comprising a current source configured to supply a given current to each of the vertical signal lines.

13. The device of claim 9, further comprising a switching MOSFET connected in series with each of the FETs between each of the horizontal signal lines and each of the vertical signal lines.

14. The device of claim 9, further comprising a diode connected in series with each of the FETs between each of the horizontal signal lines and each of the vertical signal lines.

15. The device of claim 9, further comprising a chemical state inspection section configured to inspect a chemical state of a setting region of the FETs on the basis of measurement signals of the plurality of counters.

* * * * *